United States Patent [19]
Bradshaw et al.

[11] Patent Number: 5,139,473
[45] Date of Patent: Aug. 18, 1992

[54] APPARATUS AND METHOD FOR THE REMOTE HANDLING OF HIGHLY RADIOACTIVE SOURCES IN THE TREATMENT OF CANCER

[75] Inventors: Anthony J. Bradshaw, Missouri City; Richard T. Thornton, League City, both of Tex.; Michael H. Hayman, New Orleans, La.

[73] Assignee: Omnitron International, Inc., Houston, Tex.

[21] Appl. No.: 753,192

[22] Filed: Aug. 30, 1991

Related U.S. Application Data

[62] Division of Ser. No. 596,928, Oct. 12, 1990.

[51] Int. Cl.⁵ ............................................. A61N 5/00
[52] U.S. Cl. ................................... 600/3; 600/6; 600/7
[58] Field of Search ....................... 600/1, 3, 7, 6; 250/497.1

[56] References Cited

U.S. PATENT DOCUMENTS 4,969,863 11/1990 Von't Hooft et al. ................. 600/3
5,030,194 7/1991 Von't Hooft ........................... 600/3

Primary Examiner—Francis Jaworski
Assistant Examiner—Scott R. Akers
Attorney, Agent, or Firm—Fitch, Even, Tabin & Flannery

[57] ABSTRACT

Remote controlled afterloader apparatus and method positions high activity radioactive sources through a catheter within a human body for treatment of cancerous tissue. The afterloader includes an operating console and a remotely located computer controlled wire driver. The wire driver includes active and dummy source wires and channels for the storage of such wires. Stepper motors precisely position the wires in response to computer control and data from wire position encoders. An emergency DC motor retraction system provides a high degree of safety against system malfunction. Timing arrangements are included for timing patient treatment duration and emergency wire retraction time. A turret is provided with safety locking and cross-checking systems to permit use of multiple catheters. Treatment profiles are conducted from the maximum treatment position whereby only tension or retraction forces are used to position the active wire.

7 Claims, 8 Drawing Sheets

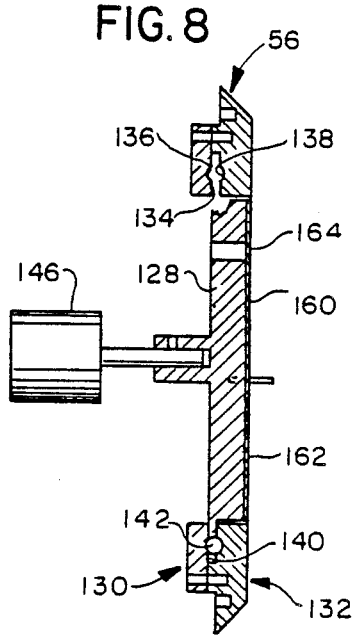
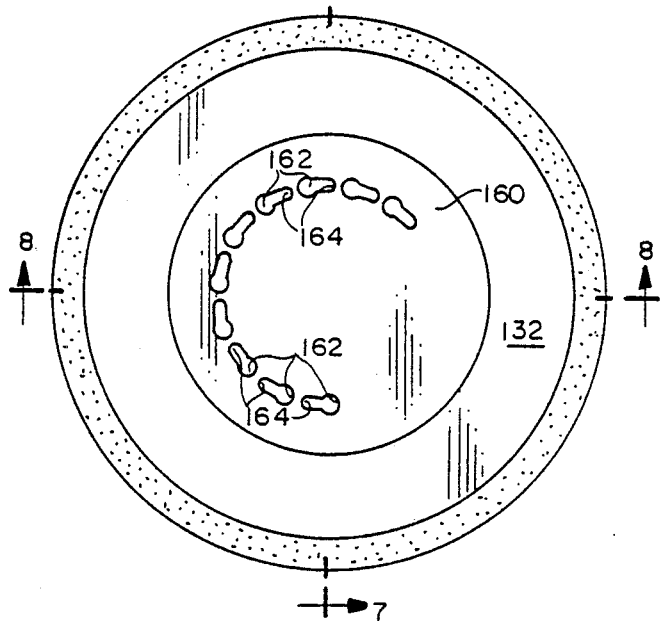
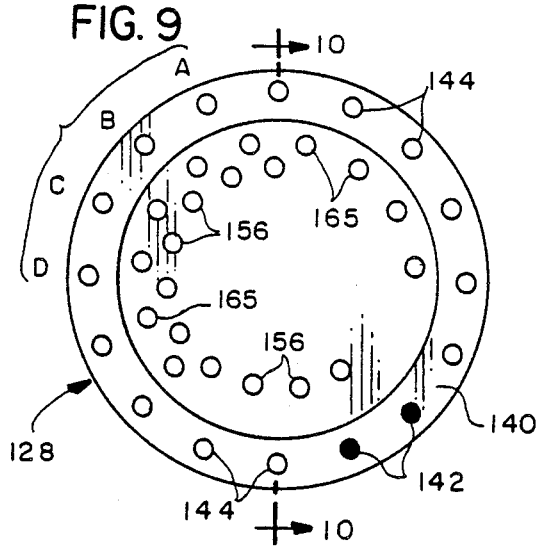
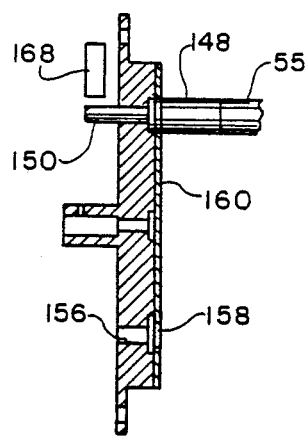
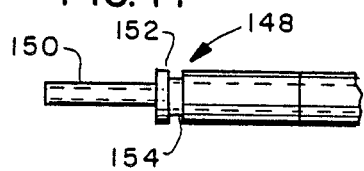

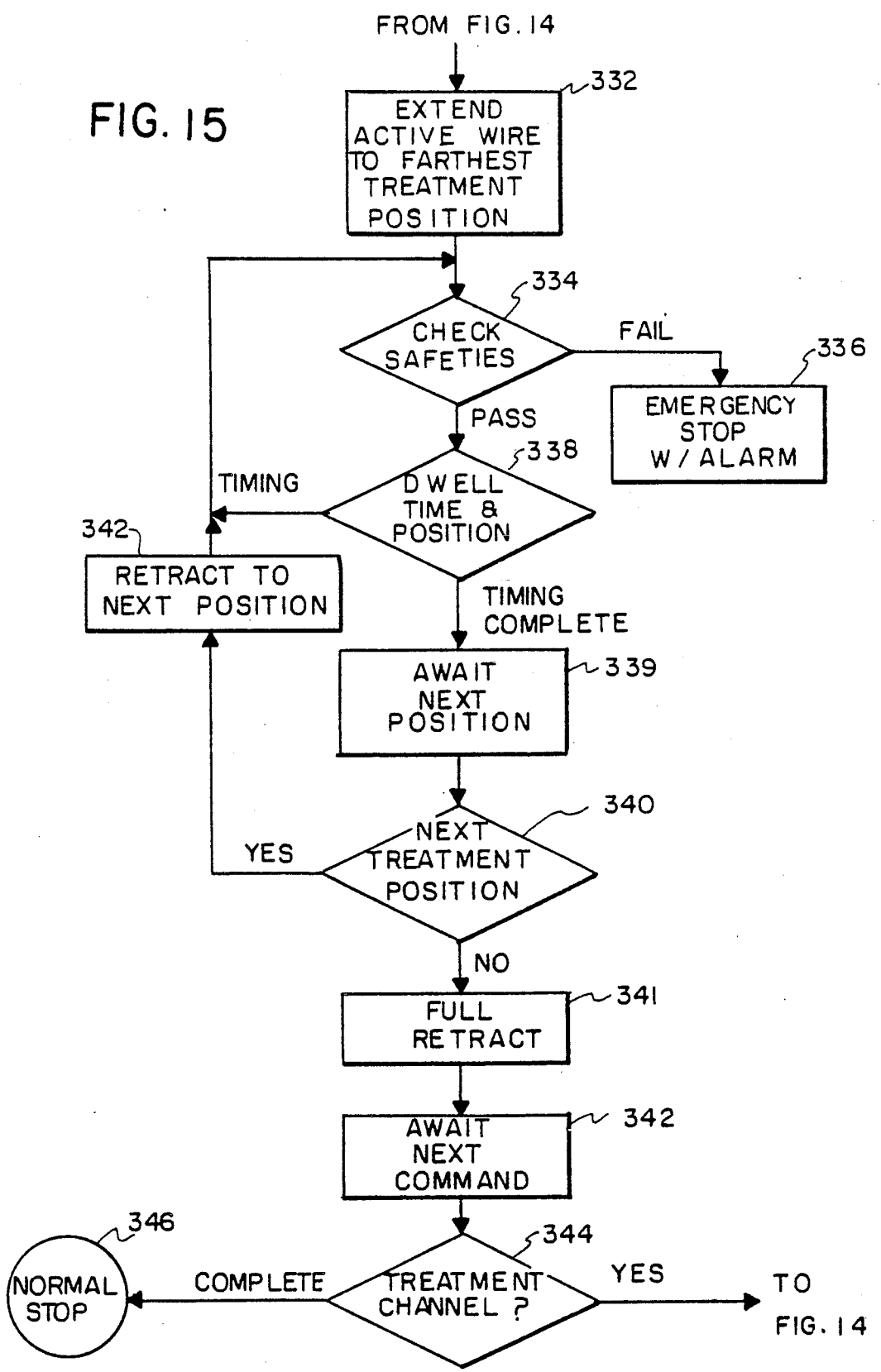

APPARATUS AND METHOD FOR THE REMOTE HANDLING OF HIGHLY RADIOACTIVE SOURCES IN THE TREATMENT OF CANCER

This is a division of application Ser. No. 596,928, filed Oct. 12, 1990.

BACKGROUND OF THE INVENTION

The present invention relates generally to methods and apparatus for the handling of high activity radioactive sources in the treatment of cancerous tissue.

The use of radioactive material in the treatment of cancer is well known in the medical field. Treatment techniques, however, vary dramatically depending upon the location of the cancerous tissue and the activity level of the radioactive source used in treatment.

One common treatment procedure involves the use of relatively low activity radioactive seeds. Due to their low activity levels, typically about 1 millicurie/centimeter, these seeds remain resident in, or adjacent to, the tissue undergoing treatment for extended periods of time, for example, several days. As a consequence, the seeds are surgically implanted, thereby allowing the patient to continue normal activities during the resident treatment period.

One of the principal advantages of such low activity treatment procedures is the ease of handling of the radioactive sources or seeds, themselves. While ordinarily stored in radioactive "safes" when not in-use, these low activity seeds may otherwise be handled freely by doctors and support personnel during implantation and removal. The disadvantages of this treatment technique, however, are long residency times and the requirement for surgical implantation and removal, the latter with its attendant trauma to adjacent normal tissue.

At the other end of the treatment spectrum are the high activity radioactive treatment procedures. These procedures, which typically employ radioactive sources in the range of 10 curies, present significant handling and treatment challenges. On the other hand, a significant offsetting advantage of such a treatment regime is its extreme speed. A complete treatment session can be completed in only a few minutes. The patient carries no radioactive implants within him from the treatment center.

A ten curie source cannot be openly handled or exposed to treatment facility doctors and personnel. Even relatively short exposures may result in radiation burns. As a consequence, high activity radiation therapy must be conducted remotely, with the radioactive source being removed from a shielded container or "safe" to the point of treatment, and thereafter returned, all by mechanical means.

It will be appreciated that apparatus for positioning high activity sources must be of uncommon integrity, accuracy, and reliability. It must have safeties, backups, and means for assuring that, in no event, can a source be lost, left behind, misplaced or, simply fail to retract into the safe, even for relatively short durations of time. The possibility for irreversible damage to normal tissue, in the time required for manual intervention upon system failure, is simply too great. As set forth in more detail below, the present invention describes a remote source afterloader having a high degree of reliability and emergency backup protection against system failure or loss of control.

The mechanical placement of high activity sources requires precise and accurate positioning both to assure proper dosage levels to cancerous tissue as well as to minimize damage to adjacent normal tissue. By reason of the intense radiation associated with high activity sources, real-time, hand-guided source placement by the treating physician is precluded. The source, therefore, is inserted through a tube, a needle, or catheter previously surgically positioned in the patient.

The use of catheters, although less invasive than the open surgical implantation of seeds, nevertheless traumatizes tissue along its path of insertion. In delicate tissue regions, for example, in the brain, such trauma must be kept to an absolute minimum. Known prior art high activity sources are affixed to the end of delivery wire of substantial diameter, typically in excess of 1 millimeter. As a consequence, the delivery wire and source must be inserted through correspondingly large tubes, needles or catheters.

Recent developments in high activity source manufacture have resulted in the availability of an ultra-thin iridium source of less than 0.5 millimeters in diameter which, in turn, permits the use of significantly narrower catheters. This source is disclosed in U.S. application Ser. No. 228,400, filed Aug. 4, 1988. In its preferred arrangement, the source comprises a 1 centimeter active region of relatively pure iridium positioned 1 millimeter from the end of 2.1 meter delivery wire. Such ultra-thin radiation sources, in combination with the present remote afterloader, now permit radiation treatment in, or proximate to, delicate tissue areas at heretofore unrealizable low trauma levels.

The present invention, therefore, is directed to a remote afterloader having the capability of properly advancing and positioning ultra-thin wire of 0.5 to 75 mm diameter with the utmost reliability and safety. It will be appreciated that these new ultra-thin source wires do not exhibit the same strength characteristics, particularly in buckling, as the more massive prior art wires. Thus, existing remote afterloader apparatus, which were developed for these heavier gauge wires, have proved unsuitable.

One such prior art device, for example, uses a drum onto which the delivery wire is wound, thereby retracting the wire from the catheter and patient. Extension of the wire, however, requires a smooth cylindrical shroud oriented around the outside of the drum against which the wire coil expands as the drum is rotated in the uncoiling direction. Upon contacting the shroud the wire is urged through a narrow opening or slit therein, then, into the catheter for delivery to a tumor site. This arrangement is wholly unsatisfactory for ultra-thin delivery wires. These wires simply do not have sufficient buckling integrity to permit the relatively unguided movement central to drum/shroud operation.

The present afterloader incorporates a dual-capstan drive arrangement in which one capstan positively feeds the delivery wire while the second capstan precisely meters wire movement. Importantly, the path of the delivery wire within the afterloader itself is tightly constrained, in both directions from the capstan drive assembly, thereby precluding buckling of the wire. More specifically, a low friction channel or tube having sufficient length to store all but the active tip region of the delivery wire is provided below the capstan drive. This channel is of minimum cross-section thereby precluding wire bending or deformation. Above the capstan drive, the delivery wire, including the iridium source, feeds into a narrow tubular structure defining the interior of a radioactive safe, then through a narrow outlet channel to a multiple catheter turret assembly. In this manner, there are no open regions within the remote driver apparatus which might permit wire buckling during either extension or retraction.

The above wire containment structure serves another extremely important safety function. It is imperative to establish that the highly radioactive iridium source portion of the delivery wire is, in fact, safely retracted and stored within the safe. Failure to properly identify a non-stored condition could result in a severe overdose to the patient and to personnel who enter the treatment environment under the mistaken belief that the source has been properly retracted.

The present afterloader, by contrast, employs redundant systems to verify proper source storage. One of these systems, importantly, provides unfailing and absolute protection against wire over-retraction. Specifically, the end of the narrow wire channel is obstructed to preclude further wire travel thereby defining a maximum wire retraction limit. This position corresponds to proper stowage of the active region within the lead safe.

Abutting engagement between the delivery wire and channel end does not, however, insure that the active region of the wire has been safely stored. For example, were the delivery wire to sever, the inactive end could properly seat against the channel end while the active region remains outside the safe, possibly still within the patient.

The present afterloader includes a console computer at which an operator can enter a treatment plan for a patient. The plan is checked by the console and high level commands specifying source position within a patient and dosage duration are sent to a remote afterloader computer. The afterloader computer receives and implements the commands by controlling wire movement apparatus. The specific actions of the afterloader as well as its safety and integrity are the responsibility of the afterloader computer.

The present invention provides absolute protection against such false indications of wire storage. In this connection, the wire guide and storage channels additionally serve to facilitate highly accurate wire length measurement. Specifically, a "home" optical wire sensor is precisely placed near the channel outlet to detect the presence or absence of the wire. When a wire is extended, the length of the wire beyond the home optical sensor, as determined from the wire movement metering capstan, is closely monitored by a wire length count maintained in the afterloader computerized controller. Upon retraction of the wire past the home sensor, the wire length count is compared with the wire length count at the home sensor when the wire was first extended. If the retraction count is different from the extension count by more than a threshold value, fault signals are generated to notify operating personnel.

In addition to the absolute and unerring determination of active element storage, it is critical that the position of the active source be known at all times with high accuracy and reliability. Improper positioning now only endangers normal tissue, but may result in the failure to treat cancerous tissue. The remote afterloader control circuitry of the present invention provides a high degree of operational cross-checking with automatic wire retraction upon cross-check failure.

Wire delivery and position determination is predicated upon the previously noted dual-capstan arrangement in which a stepper motor which is controlled by the afterloader computer drives the first capstan and a position encoder, also connected to the afterloader computer, is driven by the second capstan. Each computer controlled step of the drive motor produces a precisely known axial movement of the delivery wire and, in turn, a corresponding and known response from the encoder. The output from the encoder is compared against the stepper motor commands, both on an incremental per step basis and on an overall basis. At the incremental level, the absence of proper encoder signals following one or more steps signifies a wire jam, and further wire delivery is terminated.

The afterloader computer further cross-checks the overall number of encoder output pulses actually received against the number of expected pulses based on the number of stepper motor steps commanded. A predetermined, but small, discrepancy is permitted between the computed and actual number of drive motor steps to account for capstan slippage. However, should encoder outputs cease entirely following stepper motor actuations or should the overall number of encoder outputs not fall within the predetermined limits, it is assumed that a delivery wire jam or obstruction has been encountered. In any event, the precise positioning of the wire cannot be assured under such conditions, and, therefore, the wire will be withdrawn. Withdrawal is first attempted by controlling the stepper motor to withdraw the wire. If the stepper motor fails to satisfactorily withdraw the wire, the stepper motor and wire movement capstan are disengaged and a separate retraction motor is energized to withdraw the wire.

The delivery of high activity radioactive sources requires afterloader apparatus comprising two distinct and separately located subsystems. First, the operator console is provided. This console is located in a room separate from the radioactive source thereby avoiding exposure of treatment personnel to radioactivity while the source is extended from its safe. The second subsystem, the remote afterloader, is the mechanical source storage and delivery apparatus which receives high level commands from the console and physically feeds the active source from the safe to precise locations within the patient, and for precise time intervals.

It is a critical feature and objective of the present invention to position the source accurately within a patient and then to withdraw the source, both steps to be performed with a high degree of certainty that the source is actually where it is supposed to be. As set forth above, the described apparatus provides the requisite accuracy as long as the afterloader computer control is properly functioning.

Computers, however, occasionally malfunction. Therefore, the present afterloader provides for monitoring of proper computer function and, in the event of computer or other malfunction, for the automatic emergency retraction of the radioactive source.

The emergency retraction system functions at the most basic circuit level, thereby virtually eliminating the possibility of emergency backup system failure. In the first instance, the emergency system operates from a constantly recharging backup battery source. This backup source is constantly monitored by the computer which, in turn, signals a backup power failure, simultaneously blocking extension of the active source wire until proper backup system operation has been restored.

The emergency retraction system requires no computer control. It does not utilize the normal capstan drive stepper motors, instead, a separate DC motor driven capstan is provided. Upon primary system failure, power is switched to this motor, thereby forcing full wire retraction. Emergency retraction is timed by a retraction timer. When a retraction has taken longer than a preset time, an audible alarm is sounded to notify operating personnel. This emergency motor continues to operate until the inactive end of the delivery wire engages a switch positioned at the end of the wire storage channel.

Watchdog timers are provided within the remote wire driver subsystem to monitor the afterloader computer. In the event that valid reset signals from the afterloader computer control are not received within a preset interval, computer failure is assumed, and the automatic emergency retraction sequence is engaged. In an embodiment a redundant pair of watchdog timers is used for greater safety. Further, the timers are reset by a multi-bit binary word which follows a predetermined sequence from word to word. A received multi-bit word is compared at the timer with a predicted value and if the received word and the predicted value are not the same, the reset signal is considered invalid. A maximum treatment timer is also used which starts the emergency retraction system when the active source has been extended for more than an expected maximum treatment time.

Additional operational and apparatus subsystems are included to further assure proper overall system operation. One such subsystem is a wire delivery pretest subsystem. This subsystem assures proper active wire extension by first checking the path integrity of each catheter. This test is performed by extending a dummy wire through each catheter tracing the treatment profile intended for the active wire.

The dummy wire drive apparatus is substantially identical to that previously described for the active wire, although no emergency retraction system is incorporated. Thus, undue slippage or jamming of the dummy wire, or a failure to retract fully, signals a fault condition which precludes active wire extension. Importantly, this fault condition is registered, not merely by the computer afterloader, but in hardware interlocks of the remote wire driver apparatus itself, whereby extension of the active wire will be precluded even though the computer may have failed to register the fault condition.

A similar fault detection/protection arrangement is provided in connection with the optional multiple catheter turret. In this connection, the present invention may advantageously incorporate a turret arrangement permitting connection of up to ten separate catheters. In this manner, multiple catheters may be positioned within a patient to facilitate the more complete treatment of the cancerous tissue area in one radiation application session. Under afterloader computer control each catheter is accessed, in turn, and the appropriate pre-programmed treatment regime implemented. This regime includes the above described catheter pretesting by first extending the dummy wire.

It is imperative that no attempt be made to extend the dummy and active wires unless the turret is properly indexed at a valid catheter location having a catheter inserted therein. Consequently, detectors are provided to signal both the existence of the catheter and the proper indexing of the turret. Again, a turret or catheter fault condition is registered, not merely by the computer, but by the remote wire driver apparatus thereby assuring proper fault-induced inaction regardless of computer operation.

From the foregoing it will be apparent that the present invention provides for the control of remotely located radioactive source wire driver equipment. More particularly, apparatus for precisely positioning ultrathin sources and delivery wires is provided such that the wire may be extended from, and returned to, a safe without likelihood of wire buckling. The proper storage of the active source within the safe is determined with high reliability and the active source is absolutely precluded from over-retraction. A low friction delivery wire channel serves to guide the wire, prevent buckling, preclude over-retraction, and aid in the detection of wire breaks. Emergency backup active wire retraction is provided in the event of computer or other malfunction. Dummy wire testing of all catheters is performed. A multiple catheter selection turret may be provided. Cross-fault detection is employed to preclude active and dummy wire extensions unless the other wire is properly retracted and parked and unless the turret is properly indexed to a valid catheter position. Other features of the invention are disclosed in the following figures, written specification and Claims.

BRIEF DESCRIPTION OF THE DRAWINGS

FIG. 8 is a sectional view taken along line 8—8 of FIG. 13 of the catheter select turret assembly;

FIG. 9 is a rear elevational view of the rotating turret of the turret assembly;

FIG. 10 is a sectional view taken along line 10—10 of FIG. 9 of the rotating turret further illustrating the placement of a catheter connector therein;

FIG. 11 is a side elevational view of a catheter connector;

FIG. 12 is a front elevational view of the catheter select turret assembly showing the catheter locking plate;

FIGS. 14 and 15 are flowcharts depicting wire driver control operation; and

DESCRIPTION OF THE PREFERRED EMBODIMENT

Figure 1:
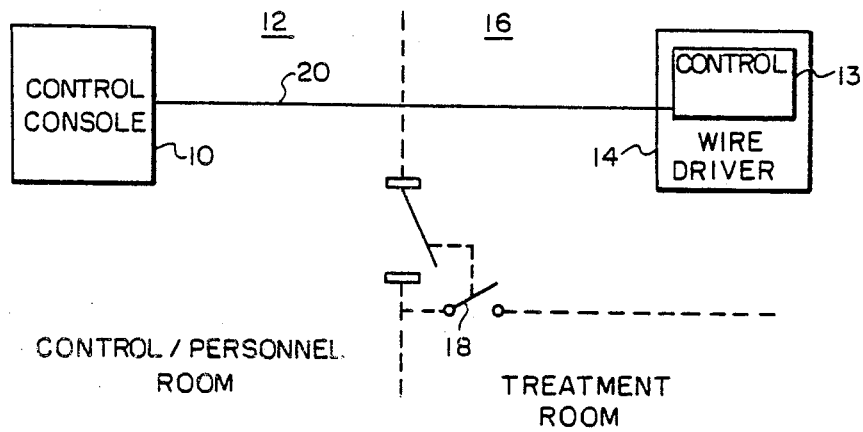
FIG. 1 is a block representation of the present wire afterloader illustrating the placement of the remote safe and wire driver in a treatment room separate from the control console.

The remote afterloader of the present invention, as shown in its most general form in FIG. 1, includes a computerized control console 10 located in a control room 12 and a remote safe and delivery wire driver 14 located in a treatment room 16. Federal regulations require, in view of the high radiation levels associated with high activity sources, that patients undergoing treatment be placed in shielded treatment rooms isolated from the attending physicians and other personnel. Thus, the treatment room 16 complies with appropriate federal regulations for shielding and, further, is provided with an entrance door interlock 18 to automatically retract, as discussed in more detail below, the active source upon entrance of non-patient personnel into the treatment room. A data and control bus 20 interconnects the console 10 with the remote dirver 14. The data and control bus 20 of the present embodiment is an RS 422 link which connects console 10 to a microprocessor controlled controller 13 of wire driver 14.

Figure 2:
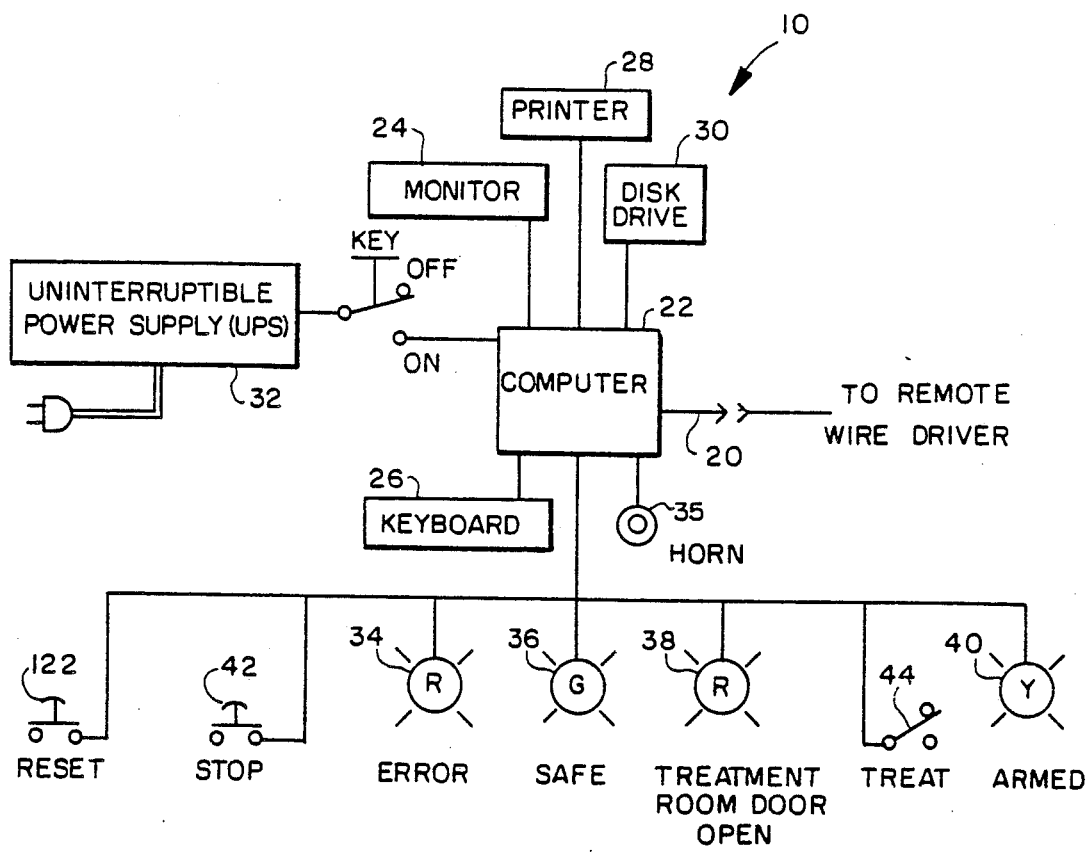
FIG. 2 is a functional block diagram of the control console of FIG. 1.

FIG. 2 is a block illustration of the control console 10 which includes a computer 22 of conventional availability incorporating a color monitor 24, a keyboard 26, a printer 28 and a floppy disk drive 30. More specifically, the computer is of the well-known 80386 processor variety and includes an additional 40 M-byte hard drive. An uninterruptible power supply 32 is provided to protect against losses of power during on-going treatment sequences. Uninterruptible power supply 32 also provides power to the wire driver 14.

Also included with the console 10 of FIG. 2 are various annunciators and specific control function input buttons. Error 34, horn 35, safe 36 treatment room door open 38, and armed 40 annunciators, as well as stop 42, treatment 44, and reset 122 keys and buttons are provided on the control console itself. A similar panel of annunciators and switches is provided at the treatment room door and at the remote wire driver. The later panels are both controlled from the wire driver controller 13.

Figure 3:
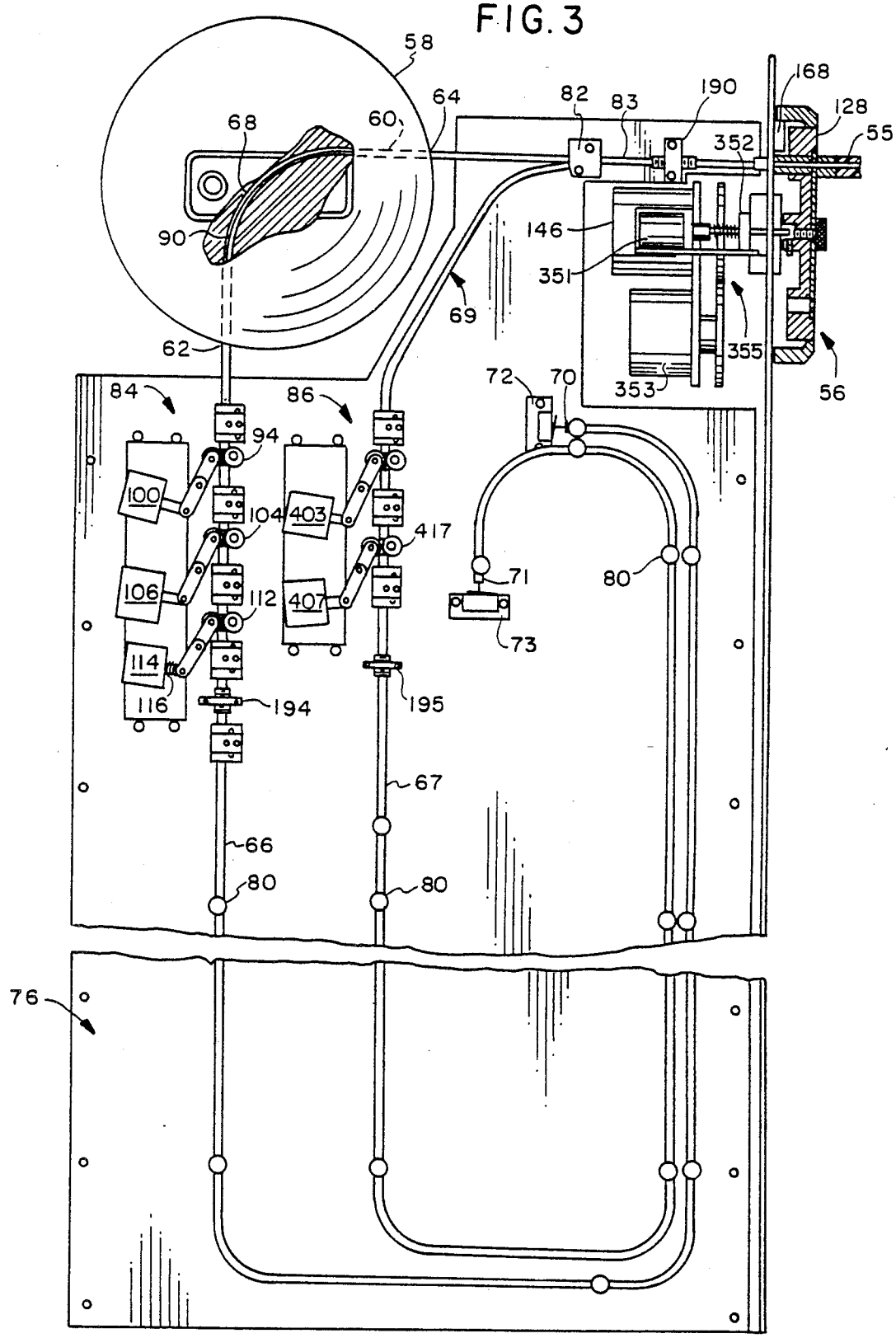
FIG. 3 is a left side elevational view of the remote wire driver of FIG. 1 with a portion broken away illustrating the placement of the active and dummy wire storage and guide channels and of wire drive assemblies and wire position detectors.

FIG. 3 illustrates various structural features of the remote driver 14 used to extend treatment wires into a catheter 55 for patient treatment. There are two delivery wires, one active and one dummy. Each is of approximately 0.5 millimeters in diameter. In the preferred arrangement, the active delivery wire has an overall length of 2.1 meters and contains a 10 millimeter long seed of activated iridium spaced 1 millimeter from the forward end thereof. The dummy wire is 1.8 meters in length and does not contain an iridium seed.

The iridium seed of the active wire is typically irradiated to an activity level of 10 curies and, therefore, represents a potentially dangerous source of radiation that must be properly stored when not in use. A lead safe 58 is provided for this purpose. In the preferred embodiment safe 58 comprises a lead sphere having a radius of approximately 106 mm. Referring still to FIG. 3, the safe 58 is provided with a 90 degree radius cylindrical channel 60 of sufficient diameter to pass the active wire source. The channel 60 defines a lower inlet 62 through which the active wire feeds from its guide and storage channel 66, discussed in more detail hereinafter, and an outlet 64 from which the active wire source is extended, thereafter, through a turret 56 and into the active catheter 55.

The active and dummy wire guide channels 66 and 67, respectively, are made of stainless steel tubes which are connected by connectors 80 to a backing plate 76. The overall length of the active channel 66 is selected such that the 10 mm active portion of the active wire 90, i.e., the iridium seed, will be substantially centered in the safe 58 at its midpoint 68 when the opposed rearward wire end abuts a park switch 72 positioned at end 70 of the active channel. In similar fashion, the overall length of dummy guide channel 67 is selected such that the forward end of the dummy wire will be retracted to a non-interfering position 69 when the opposed rearward end thereof abuts a dummy park switch 73 at channel end 71. The channels 66 and 67 are broadly radiused, preferably to about 80 mm, to minimize wire friction therewith.

It should be note that other channel constructions are contemplated by the present invention. Any construction providing for the low friction storage of a predetermined length of delivery wire, and without substantial openings or volumes into which the wire might buckle, should be satisfactory.

Referring to FIG. 3, the respective active and dummy wire channels merge in a "Y" or wishbone channel connector 82, thereafter forming a single output channel 83 operatively interconnected with the turret 56. The wishbone connector 82 is milled to the ultimate channel working dimension through which the respective active and dummy wires pass directly.

Figure 4:
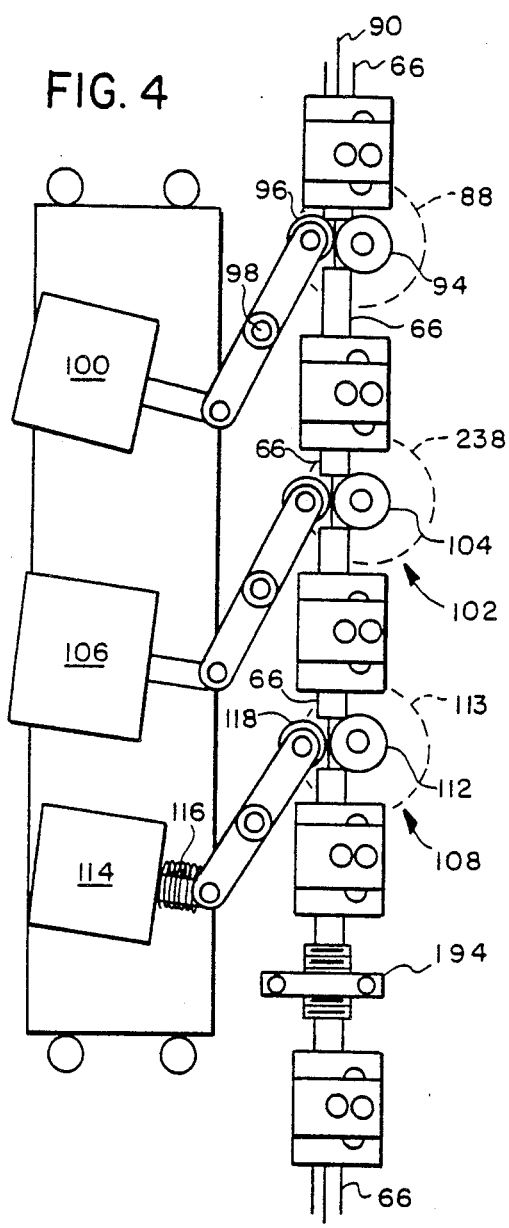
FIG. 4 is an expanded view of the wire movement apparatus of FIG. 3.

The active wire drive and emergency retraction system 84 is shown in FIG. 3 and in enlarged form in FIG. 4. The dummy wire drive system 86 is identical, except that the emergency retract motor 113 and its drive assembly 108 is omitted. The uppermost capstan 94 and pinch roller 96 define the stepper motor 88 wire drive assembly. Stepper motor 88 is beneath backing plate 76 and is shown in dotted lines. Under computer stepper control from wire driver control 13, stepper motor 88 moves the active wire 90 along the previously identified path 66 in both the extension (upward) and retraction directions. As described in more detail below, the active wire is extended to the maximum treatment position then, as required by the prescribed treatment profile, retracted in precisely timed intervals of predetermined distance until the entire treatment cycle for the given catheter has been completed.

As shown in FIG. 4, the stepper motor 88 drive assembly includes a rubber surfaced capstan 94 which is rotated by the stepper drive motor 88. A rubber pinch roller 96 is pivotally mounted at a pivot 98 and urges active wire 90 against the capstan 94 when pull-type solenoid 100 is energized. As can be seen in FIG. 4, sections of the guide channel 66 have been removed so that the pinch roller 96 and capstan 94 can physically contact the drive wire 90. The remaining sections of channel 66 guide the wire 90 so that it remains substantially straight and runs parallel to the plane of capstan 94 rotation.

Below the drive capstan 94 is the encoder drive assembly 102. It is substantially identical to the above described wire drive assembly except that an encoder 238 which is connected through plate 76 to an encoder shaft or capstan 104 is substituted for the stepper drive motor 88. When active pull-type solenoid 106 is energized and moves a pinch roller to engage the wire 90 with capstan 104, movement of the wire 90 rotates capstan 104. Encoder 238 responds to the rotation of capstan 104 by sending wire movement indicating pulses to controller 13 which uses the pulses to track the position of the active source in wire 90.

The lowest capstan, used only in connection with the active wire drive and retract system 84, defines the emergency retract assembly 108. This assembly differs from the stepper motor drive assembly in two important aspects. First, the capstan 112 is driven from a conventional, non-stepper type DC motor 113. Second, the pinch roller controlling solenoid 114 is of the push-type and includes a spring 116 which biases a pinch roller 118 against the capstan 112. Solenoid 114 power is required to retract the pinch roller 118 thereby disengaging the wire 90 from the emergency retract capstan 112. In the event of a computer failure, power failure, or other system loss of control, power is dropped to emergency retraction solenoid 114, thereby automatically engaging the wire 90 with emergency retraction capstan 112, while emergency battery power is simultaneously applied to emergency retraction motor 113. As this is a conventional DC motor, no special control or stepping instructions are required. Emergency retraction may be effected even through other portions of the afterloader system, including the computer 22 and controller 13 are inoperative.

Figure 16:
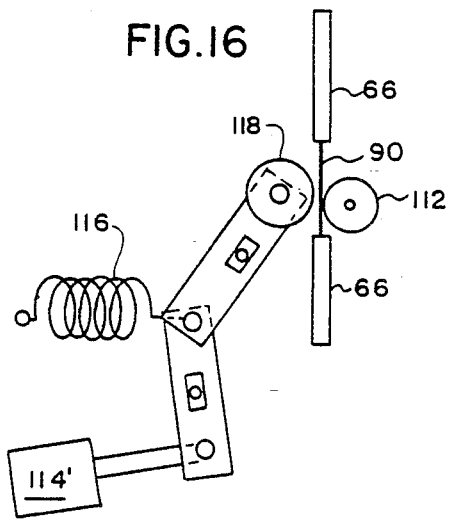
FIG. 16 is an alternative embodiment for a pinch roller control assembly of FIG. 4.

Alternatively, emergency retraction assembly 108 could be constructed using a pull-type solenoid 114' and a jointed pinch roller control arm as shown in FIG. 16. In FIG. 16 components performing the same function as in FIG. 4 are given the same reference number.

Two over-travel optical sensors provide an additional level of protection and redundancy to the system These sensors 194 and 195 (FIG. 3) are mounted along respective active and dummy wire channels 66, 67 immediately below the wire drive systems 84 and 86. The computer control system is pre-programmed to accept a maximum treatment profile well below the 2100 mm length of the active wire, e.g., 1500 mm, thereby assuring that some portion of the wire will always remain adjacent the respective over-travel sensor. Therefore, the detection of a "no wire" condition by either overtravel sensor 194, 195 necessarily signifies system malfunction terminating treatment and mandating emergency active wire retraction.

An additional optical sensor 190, called the home sensor, is placed in channel 83 to detect the presence and absence of a delivery wire. The home sensor 190 is the index point against which source positioning is measured. The home sensor is used to detect when a drive wire tip passes the home sensor point both on extension and retraction. Sensor 190 transmits signals indicating the presence or absence of a wire at the home position to control 13.

The catheter turret 56, which is shown in FIGS. 7 through 12, comprises a turret 128 (FIG. 8) retained for rotating movement between inner and outer race members 130 and 132, respectively. Race members 130, 132 are rigidly affixed to the housing of the remote wire driver 14 and define an annular channel 134 therebetween. A pair of radius grooves or races 136 and 138 are formed in opposed channel surfaces of the race members.

An annular flange 140, integrally formed on the perimeter of turret 128, is received within the channel 134. A plurality of ball-type bearings 142 are seated within holes 144, which holes are evenly spaced around the turret flange. Bearings 142 travel within races 136, 138 thereby permitting the smooth rotation of the turret 128 under the computer driven control of a stepper motor 146 attached thereto.

Placement and locking of catheters 54 into the turret assembly 56 is best illustrated in FIGS. 8-12. As shown in FIG. 11, the end of each catheter is provided with a connector 148 defined, in part, by a cylindrical extension member 150, an annular locking flange 152 and a recess 154. A plurality of complementary catheter receptacle holes 156 are evenly spaced (FIG. 9) around a diameter of turret 128. Each hole includes a region of widened diameter 158 (FIG. 10) adapted to receive a catheter locking flange 152 therein.

A circular catheter locking plate 160 is mounted adjacent the outside of the turret 128 for limited rotation with respect thereto. As shown in FIG. 12, the locking plate 160 is provided with a plurality of holes 162, with narrowed annular extensions 164, the holes having spacings corresponding to those of the catheter holes 156 in the turret. Thus, the locking plate may be rotated to admit passage and positioning of one or more catheters in the turret. Following catheter insertions, the locking plate 160 is rotated until the narrower annular extensions 164 are received within catheter connector recesses 154 thereby locking all catheters against inadvertent removal.

It is essential to establish the existence of a catheter in the active catheter position 55 as a prerequisite to wire extension, particularly extension of the active wire. The active catheter position is defined by the uppermost hole 156 of the turret 128, so long as that hole is properly aligned immediately above the turret/stepper motor axis. In this position, a wire extended from the output channel 83 (FIG. 3) directly enters the active catheter 55 mounted adjacent thereto.

FIG. 10 illustrates the orientation of a catheter 54 in the active catheter position 55 An optical catheter-inplace sensor 168 is mounted to the fixed inner race 130, immediately above the active catheter position. Optical sensor 168 includes an optical source, pointed downward and an optical receiver for receiving reflected light from beneath the sensor. When the cylindrical tip member 150 of a catheter connector extends inwardly from the turret, light from the source of optical sensor 168 will be reflected and returned to the receiver. A signal indicating the receipt of reflected light is sent to control 13.

Figure 7:
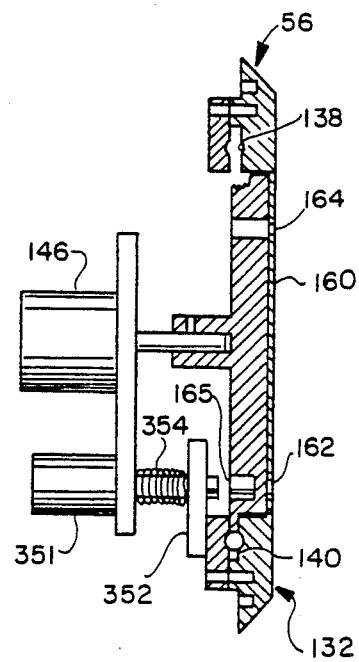
FIG. 7 is a sectional view taken along line 7—7 of FIG. 13 of the catheter select turret assembly.

Before the wire is extended into a catheter, it is important to assure that the turret 128 will not rotate during treatment. The inside face of turret 128 includes a plurality of cylindrical locking apertures 165 (FIG. 9), which are angularly spaced the same as catheter receiving holes 156, but rotated from the catheter holes by approximately 90°. As shown in FIG. 7, the turret assembly includes a locking solenoid 351 which is structurally connected to the turret drive assembly. Solenoid 351 has a shaft 354 which is of suitable diameter to engage the holes 165. When a catheter is placed in the active position 55, solenoid 351 is energized to thrust shaft 354 into a hole 165. Advantageously, the outward end of shaft 354 may be tapered to promote engagement with a hole 165 and to slightly correct the position of the active catheter. The assembly of FIG. 7 also includes an optical sensor 352 which, by means of an aperture (not shown) in shaft 354, senses the seating of shaft 354 into turret 128. A signal representing such seating is sent from optical sensor 352 to control 13.

Turret 56 is rotationally positioned by the cooperative action of a stepper motor 146 and a rotation sensing optical encoder 353 (FIG. 3) rotationally coupled at 355 to the stepper motor. Encoder 353 transmits to wire drive control 13 a series of signals indicative of its rotation and sends an index position signal once per 360° rotation. The index position signal, which is common to rotational encoders, is used to align the components of turret 56 during assembly and to identify a "home" catheter aperture 156 at the beginning of each treatment. During assembly, the turret shaft is rotated until the index signal is generated by encoder 353. The turret 128 is then mounted to the shaft with a first (home) catheter hole aligned with the output of guide tube 83. Thereafter, the index signal from rotational encoder 353 is used to identify the home turret position.

When turret 128 rotation is desired, control 13 sends stepper pulses to stepper motor 146 until the index signal is generated by encoder 353. The number of stepper control pulses between the home catheter position and the destination catheter position, can then be sent to stepper motor 146 to achieve the proper rotation to place the destination catheter at the active location. The output signals from encoder 353 are used by control 13 during such rotation to check the actual turret rotation accuracy.

Treatment begins when an operator enters, at console computer 22, a treatment plan for a particular patient and the catheters connected to that patient are attached to the connectors 156 of turret 56. The treatment plan specifies which turret connectors, i.e., which catheters, are to receive treatment, the location of treatment in distance from the home sensor 190, and the length of time for each treatment. After entry of the plan, console computer 22 runs diagnostic tests, checks the treatment plan for accuracy and safety.

Figure 5:
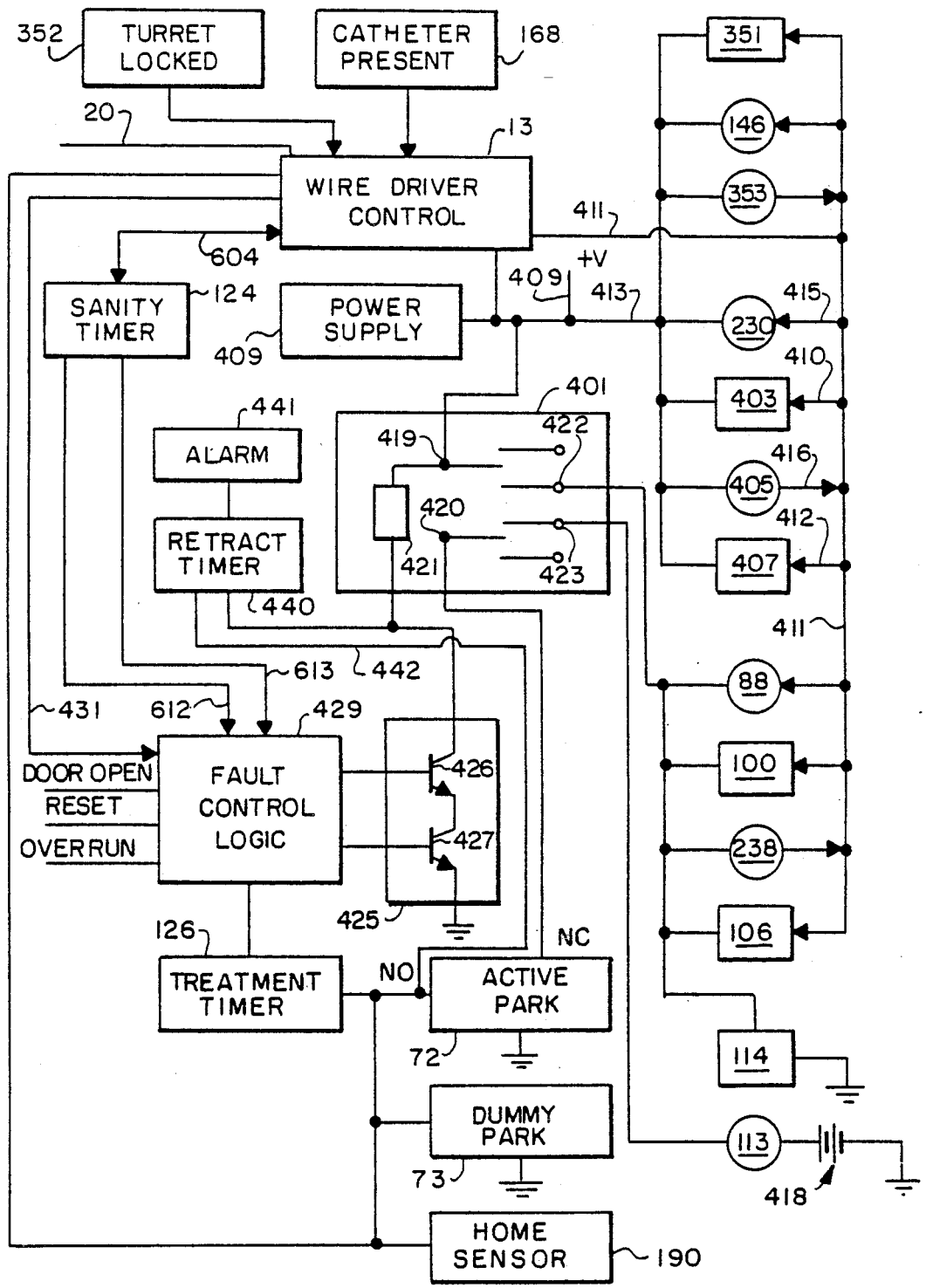
FIG. 5 is a block diagram of the wire driver control circuitry.

After safety checks by the console computer 22, it transmits a message over RS422 link 20 to wire driver control 13 of remote wire driver 14. FIG. 5 is a block diagram of the control circuitry included in wire driver 14. The message on link 20 is received by controller 13 of the remote wire driver 14 which in response, performs a number diagnostic and safety tests within remote wire driver 14. A response message is then returned to computer 22, indicating the success of the tests. Console computer 22 then responds by identifying the first turret connector (catheter) which is to receive treatment. Wire driver 14 responds to this message by checking to see that both the dummy and the active wires are in their fully withdrawn positions as indicated to control 13 by the signals from active park switch 72 and the dummy park switch 73. Wire driver control 13 then transmits stepper motor control signals on a multi-conductor bus 411 to stepper motor 146 to first "home" the turret then place the first treatment catheter, e.g., 55 in the active position to receive the active or dummy wire from wire driver 14. As stepper motor 146 rotates the turret, the turret motion is sensed by encoder 353 and reported via bus 411 to wire driver control 13 which tracks the rotation. When catheter 55 is in the active position, wire driver control 13 transmits an activation signal to solenoid 351 which drives the locking pin 354 into place. Wire driver control 13 then checks locking pin detector 352 and catheter present detector 168 to determine if the turret is properly locked in place and if a catheter, e.g., 55 is in the active turret position.

In order to properly check the safety of the treatment, the console computer 22 next sends a command specifying that the non-radioactive dummy wire is to be moved to the maximum treatment distance and withdrawn. Wire driver control 13 responds to the command by grounding dummy wire drive solenoid 403 and dummy wire encoder solenoid 407 over conductors 410 and 412, respectively, of multi-conductor bus 411. The other terminals of solenoids 403 and 407 are permanently connected to a positive voltage supply 409 via a conductor 413. Accordingly, both solenoids 403 and 407 are energized to engage the dummy wire between their respective pinch rollers and capstans. Wire driver control 13 also begins to transmit stepper motor control signals over communication path 415 of bus 411 to advance the dummy wire by rotating dummy wire stepper motor 230.

As the dummy wire moves, it rotates capstan 417 of dummy wire encoder 405. The movement of capstan 417, and thus the movement of the dummy wire, is detected by encoder 405 and reported to wire driver control 13 over path 416 of bus 411. Wire driver control 13 stores a wire position value and continuously updates this value in response to the signals from encoder 405. Control 13 also surveys the rate of wire movement signals from encoder 405 to make sure that the dummy wire is moving at substantially the same rate that stepper driver 230 is being commanded to move it. Should the wire not be moving at an appropriate rate, slippage is indicated and stepper motor 230 is commanded by wire driver control 13 to reverse and thereby retract the dummy wire.

Assuming that the dummy wire is advancing at an appropriate rate, it will shortly be connected to guide tube 83 by connector 82 (FIG. 3) and passed through home sensor 190. Home sensor 190 is an optical sensing means which detects when the tip of a wire, either the active wire or the dummy wire passes therethrough. When the wire passes through home sensor 190, wire driver control 13 records a count called the home count which represents the wire position value when the tip of the wire passed the home sensor. As the wire continues to move into and out of the catheter, the wire position value is incremented and decremented in response to signals from encoder 405.

Console computer 22 specifies treatment positions in terms of distance from the input of the catheter (output of the wire driver). A known guide tube distance, called the offset, exists between the home sensor to the wire driver outlet. Due to the offset, a treatment distance specified in a command is reached when the wire movement value, minus both the home count and the offset, equals that specified treatment distance.

The dummy wire continues to advance through the turret into the treatment catheter 55 until the maximum treatment distance has been reached by the tip of the dummy wire. Wire driver control 13 then reverses the direction of rotation of stepper motor 230 to begin withdrawing the dummy wire back into wire driver unit 14. When the tip of the wire again passes home sensor 190 in the withdrawal direction, wire driver control 13 is notified. The amount stored in the wire position value should be substantially equal to the home count which was recorded when the dummy wire interrupted sensor 190 during the wire extension operation. If these numbers are within a predetermined threshold of one another, the process is assumed to be accurate and the dummy wire continues to be withdrawn until it parks against park switch 73. Wire driver control 13 is notified when the dummy wire changes the position of park switch 73 and ground is removed from the solenoids 403 and 407. Also, no new control signals are transmitted to stepper motor 230. After the proper operation of the treatment apparatus is determined by the extension and withdrawal of the dummy wire, wire driver control 13 is ready to perform the requested treatment using the active source wire 90. Active wire 90 movement is performed substantially as described above except that the drive apparatus 84 of the active wire is used.

Due to the increased hazards involved in extending the radioactive wire 90, an emergency shutdown and wire retraction system is included in the apparatus of FIG. 5. A safety relay 401 is the heart of the emergency shutdown and active wire retraction system. Upon the automatic detection of any system abnormality or difficulty, or upon the manual intervention by a system operator through the actuation of a stop button, the relay 401 is immediately de-energized and remains de-energized until the cause of the problem has been corrected and the operator resets the system. When relay 401 is de-energized power is removed from the stepper motor control portion of active drive assembly 84 and retraction motor 113 is energized to withdraw the active wire 90.

The relay 401 is directly interconnected with both the emergency retraction DC motor 113 and to the emergency retraction capstan solenoid 114 thereby instantly commencing the emergency retraction cycle. Upon relay 401 deactivation power is removed from the retraction solenoid 114 and power from the emergency backup battery 418 is applied to the emergency retraction motor 113. The emergency retraction cycle continues until the active wire 90 is fully retracted, as determined by wire engagement with the park switch 72.

Relay 401 includes a plurality of stationary contacts 422 and 423, a pair of movable contacts 419 and 420 and a coil 421. Coil 421 is energized for normal operation by connection to the power supply 409 and to ground via a fault interrupter circuit 425. Fault interrupter 425 comprises a pair of transistors with their emitter-collector paths serially connected. Both transistors, in normal operation, receive from fault control logic 429 high level signals at their bases so that low resistance path is presented from coil 421 to ground. When coil 421 is energized, armatures 419 and 420 of relay 401 are pulled down so that armature 419 connects power from power supply 409 to stationary contact 422 which is connected to active drive stepper motor 88, active drive enable solenoid 100, encoder 238, encoder solenoid 106 and emergency retract solenoid 114. While relay 401 remains energized, the active wire drive is capable of moving the active wire 90 as directed by wire driver control 13 and retraction solenoid 114 is energized to release any engagement with active wire 90.

When a fault occurs, fault control logic 429 removes the high level signal from the bases of one or both of the transistors 426 and 427, de-energizing relay 401. In the de-energized state, the armature of relay 401 moves up and contact 420 touches contact 423 which is connected to the minus or ground terminal of DC retraction motor 113. The positive terminal of retraction motor 113 is directly connected to battery 418. Contact 420 of relay 401 is connected to ground via the normally closed contact of active wire park switch 72. Should relay 401 be de-energized while active wire 90 is extended, power is removed from the active wire stepper drive 84 including the retraction solenoid 114 and ground is applied to retraction motor 113 via relay 401 and active park switch 72. Releasing solenoid 114 engages the DC retraction capstan 112 with active wire 90, and grounding the motor 113 starts the retraction operation. When the end of active wire 90 presses park switch 72, the active wire is safely stored in the drive apparatus and the ground connection is removed from motor 113 to stop its retraction operation.

A timer 440 is activated during each emergency retraction to time the retraction and cause an audible alarm when the retraction is not completed within approximately 30 seconds. Retraction timer 440 is normally kept idle by the low level signal at the collector of transistor 426. When this collector goes high, as will be the case when relay 401 is de-energized, timer 440 begins to time a 30 second interval. The return of active wire 90 into contact with park switch 72 generates a reset signal which is connected via conductor 442 to timer 440. The reset signal on conductor 442 will clear timer 440, if it is received within the 30 second time out interval. If it is not received within the 30 second interval, a signal is sent from retract timer 440 to an alarm 441 which notifies operating personnel by means of an audible alarm signal.

Fault control logic 429 responds individually to a plurality of fault signalling conditions by removing the high level signals from the bases of transistors 426 and 427. Among the signals which result in de-energizing relay 401 are signals from door open switch 18, a reset switch on the control panel of wire driver 14 (not shown) overrun detector 194, and signals requesting retraction received from control 13 on a conductor 431. Fault control logic 429 also de-energizes relay 401 in response to signals from a pair of activity timers 124 and 126.

The first of the activity timers, timer 124, monitors the ability of wire driver control 13 to function. Control 13 transmits a periodic signal on a bus 604 approximately once every 100 milliseconds, but only when the computer hardware and software are functioning properly. If this signal is lost for more than about 100 milliseconds, the timer 124 sends a fault signal to fault control logic 429 which, in turn, releases the relay 401.

Figure 6:
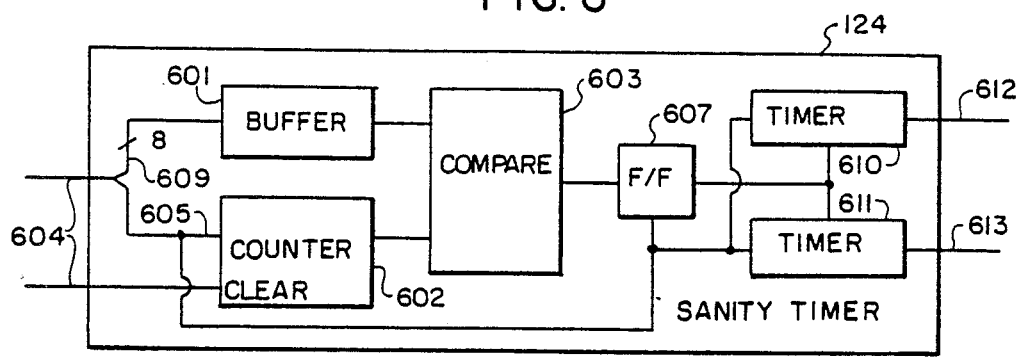
FIG. 6 is a block diagram of a sanity timer of FIG. 5.

The activity timer 124 actually comprises a pair of redundant 100 millisecond timers 610 and 611 (FIG. 6). Unless reset every 100 milliseconds by signals from control 13, each timer 610 and 611 will generate a time-out signal on a respective one of conductors 612 and 613. Such time-out signals are connected to fault control logic 429 and cause de-energization of relay 401.

The reset signals from control 13 comprise 8 binary digits and a strobe signal. To constitute proper reset signals, a given reset signal must be exactly one greater than the immediately preceding reset signal. The 8 bit reset signal portion is received on path 609 of bus 604 and stored in a buffer 601, the outputs of which are applied to an 8 bit comparator 603. Timer 124 also includes an 8 bit counter 602 which counts modulo 256, the incoming strobe signals which are connected to counter 602 via path 605. The outputs of counter 602 are also applied as inputs to comparator 603 where the counter bits are compared with the contents of buffer 601. When the compared values match, which they should during normal operation, a logic 1 reset signal is transmitted by comparator 603 to a flip-flop 607 which buffers the reset signal and conveys it to timers 610 and 611 before they time out. Alternatively, when the values of counter 602 and buffer 601 do not match, indicating system error, a logic 0 signal is generated by comparator 603 and timers will transmit fault signals to fault control logic 429 when they time out. The counter is initially synchronized with the reset signals from control 13 by a clear signal transmitted to counter 602 on bus 604. The requirement that the 10 millisecond reset signals follow a prescribed sequence provides great assurance that control 13 is functioning properly.

The second activity timer 126 commences timing whenever the active wire 90 is extended. That is, whenever the active wire is not pressing the active park switch 72. A maximum time of about 20 minutes is allotted for active wire extension which time limit exceeds the duration of the longest treatment profile anticipated. Failure of the active wire to return to the parked position at least once every 20 minutes indicates a problem necessitating emergency active wire retraction.

For the purposes of the treatment timer 126 oversight, the park switch 72 signals the full retraction or parking of the active wire. In the absence of the required park signal within the predetermined time limit, the timer 126 signals fault control logic 429 which releases relay 401.

It will be appreciated that the above described run safety relay 401 system provides a highly reliable means for forcing the immediate retraction of the active wire 40 in the event of computer or other failure. Importantly, this system is self-contained on the remote driver 14 chassis; and is of simple design thereby minimizing likelihood of failure; and incorporates backup power to further eliminate the possibility of emergency retraction failure.

Figure 13:
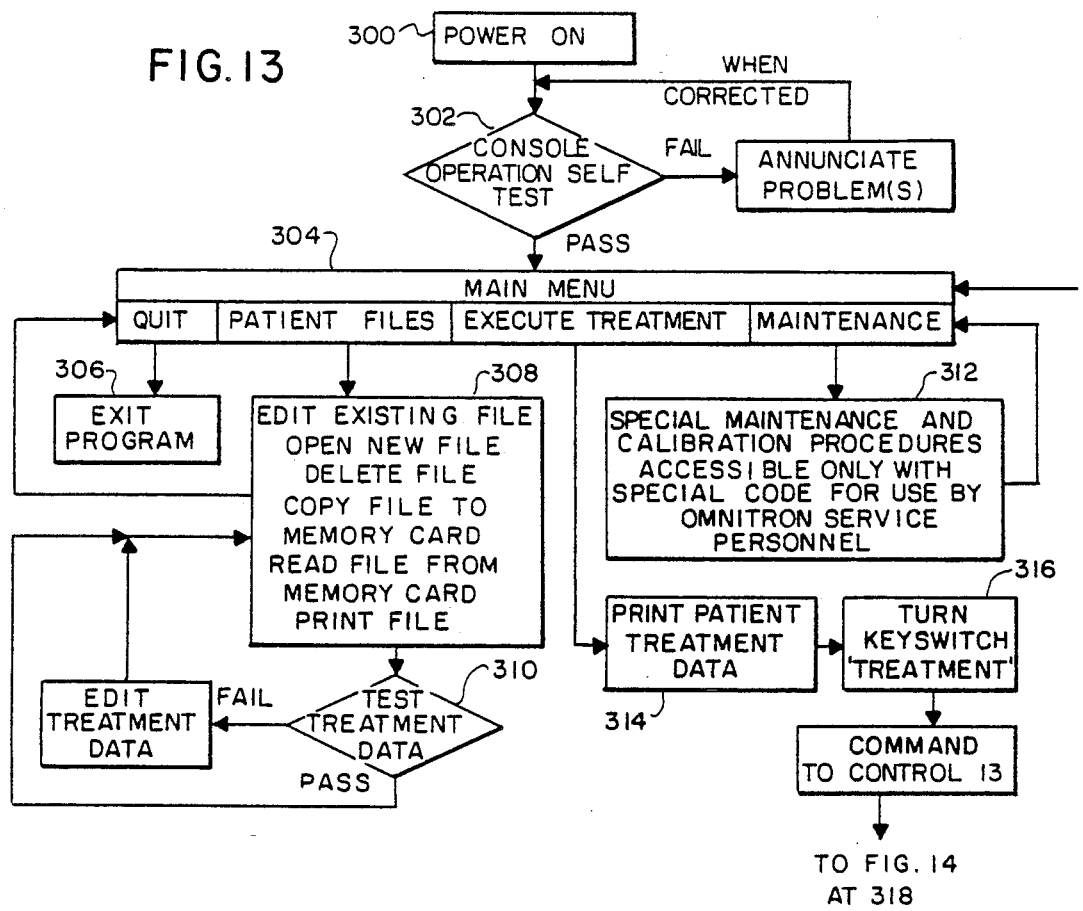
FIG. 13 is a flowchart depicting console computer operation.
Figure 14:
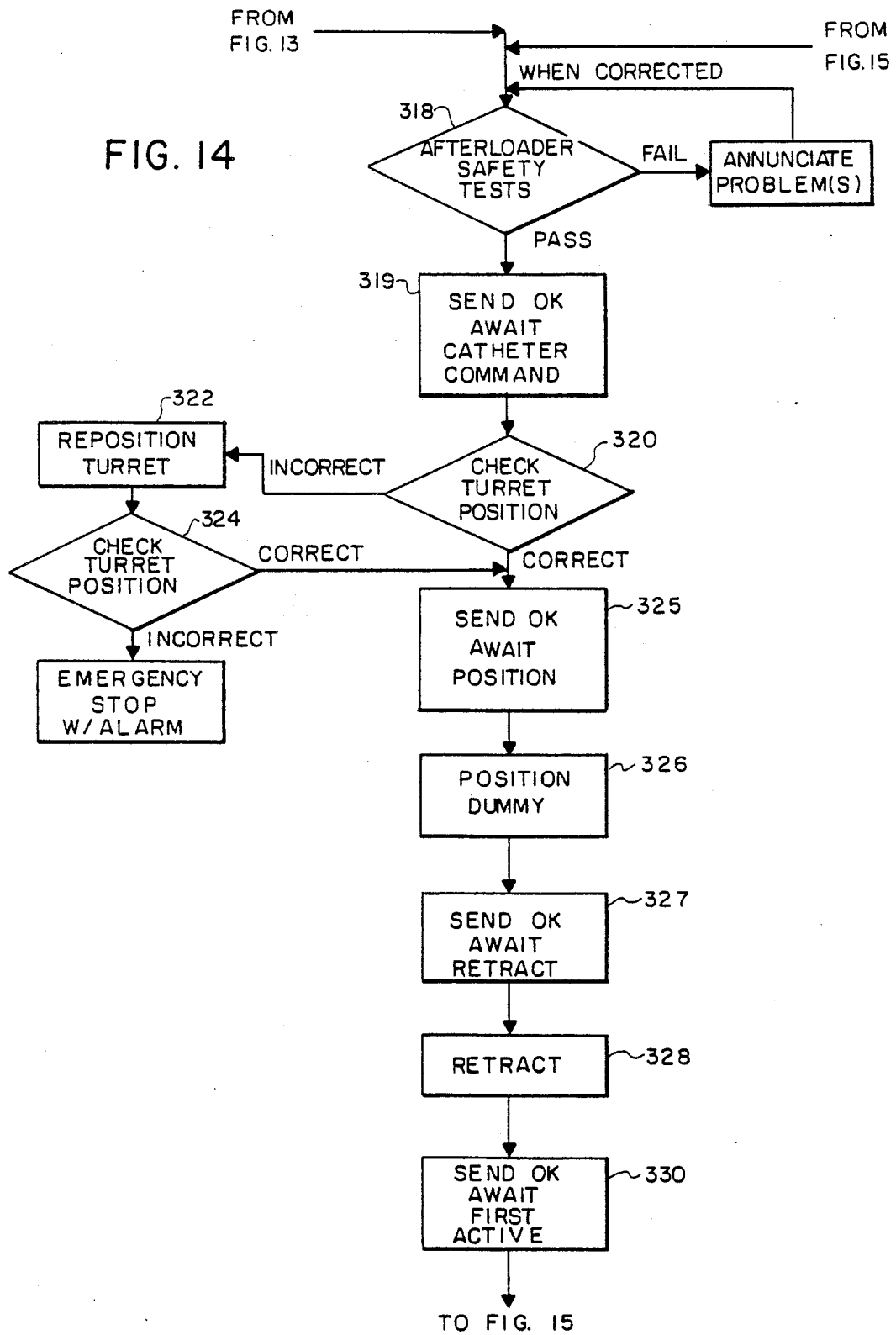

FIGS. 13 through 15 illustrate overall computer controlled operation of the present remote wire afterloader system. Upon system power-up 300 and initial console self-test 302, a main menu 304 permits optional courses of action including exiting the program 306 thereby permitting use of computer 22 for other tasks.

Patient treatment information, including the proposed treatment profile, must be entered 308. Such profiles typically include a listing of each treatment position, by distance measured from the catheter outlet of wire driver 14, as well as the treatment dwell time at each such position.

This information is checked 310 to verify, for example, that the selected profile does not violate system or medically based operational rules. Specifically, in its present and preferred arrangement, profile parameters must not include treatment positions exceeding 1500 millimeters or position dwell times exceeding 60 seconds. Further, the dwell positions must be arranged in descending order and not be closer together than a predetermined distance as specified during system initialization, i.e., at 312.

The requirement for descending order dwell positions is important to proper operation of the present afterloader particularly in view of the extremely fine diameter wire for which the present system is intended to operate. Notwithstanding the dummy wire pretesting of each catheter to verify that an ultra-thin wire can be moved to the requisite dwell positions, there always remains some possibility than an ultra-thin wire will become jammed precluding further inward movement.

On the other hand, once a wire has been inserted to its maximum treatment position, the likelihood of jamming upon the retraction of that wire is extremely small. Therefore, it is preferable to commence treatment at the maximum dwell position whereby the active wire may immediately be retracted should the computer detect undue wire slippage at the drive capstan. This condition, as noted, is sensed by comparing the rate of wire movement detected by the encoders e.g., 238 with the rate of wire movement requested of the stepper motors e.g., 88.

A maintenance capability 312 is accessible to qualified personnel for the purpose of source loading, unloading, calibration, and the setting of treatment profile parameter limits such as maximum dwell time and minimum dwell step sizes.

A patient treatment record, including proposed treatment profile, is printed 314 prior to each treatment session. Actual initiation of a treatment session requires actuation of a key switch 316 by the doctor or other personnel having appropriate authority.

The computer 22 then transmits an enable treatment command to control 13. The control 13 then performs a number of safety tests 318 (FIG. 14) in response to the enable command. Specifically, the control 13 verifies at 318 that the treatment room door is closed; that the console-to remote driver communications bus 20 is functioning; that both active and dummy wires are parked; that the wire position sensors are functioning; and, that the emergency backup battery voltage is proper.

After satisfactorily passing the tests of 318, wire driver control 13 returns a command completed or OK message to computer 22 at block 319 and awaits the next command which will be a catheter select command, specifying a catheter location. Upon receipt of the catheter command, the turret position is set and checked at 320 by "homing" the turret, controlling stepper motor 146 to rotate to the specified position and locking the turret 128 by the solenoid 351. The turret is repositioned at 322 and rechecked at 324 if the initial position is not correct. During steps 320 and 324 the turret is also checked for the presence of a catheter in the selected position.

In step 325, another command complete message is sent to computer 22 and wire driver control 13 awaits a dummy position command specifying a dummy wire position in block 325. When the dummy position command is received, wire driver 14 tests the first catheter position by cycling the dummy wire at 326. The wire driver control 13 selects the dummy wire by grounding drive solenoid 403 and outputting a series of stepper motor commands sufficient to move the dummy wire approximately 5 millimeters beyond the dwell location specified for the catheter under test.

More specifically, the driver control 13 first calculates the number of steps required to extend the wire to the desired maximum position (including the 5 millimeter overextension) and the corresponding number of pulses expected from the dummy wire encoder 405. These calculations are based on a reference point defined by the home optical sensor 190, located adjacent the turret. Stepping of the dummy stepper 230 motor now commences and continues until the specified dummy wire position is achieved.

During dummy wire extension, the control 13 is performing cross-checks to verify that no obstructions or jams have been encountered. First, wire jams are determined by comparing the number of encoder 405 pulses received per stepper motor step. Advantageously, this test may be performed only after a predetermined number of steps have been taken to save computer resources. In the present embodiment, such a comparison is performed after each block of 33 stepper motor steps. If pulses stop, or fall below the expected rate, the wire is retracted and a jam condition is annunciated.

After achieving the specified dummy wire position, wire driver control 13 sends an OK signal, and awaits a retraction signal at 327. The dummy wire is fully retracted in block 328 to terminate the dummy wire test cycle. Upon retraction, the length of the dummy wire is again checked to confirm that the wire has not broken.

This check is performed by comparing the stored home count with the wire movement value which should be substantially equal. The wire driver control 13 signals the successful completion of retraction to computer 22 and awaits an active wire command in block 330.

The active wire command from computer 22 specifies the maximum treatment position for the active wire. The active wire is then extended to the furthest treatment position at 332 (FIG. 14). Extension of the active wire is substantially identical to that of the previously described dummy wire. The wire is then precisely positioned at the first treatment location by, as before, first over-extending the wire by approximately 5 millimeters. Wire jamming and obstruction tests are performed again, as outlined with reference to extension of the dummy wire.

During the treatment phase, the control 13 continues to monitor system safety indices at 334, including the long term watchdog timer 126. Since the active wire is fully retracted and parked between each catheter treatment profile, this timer reflects active wire extension beyond the maximum treatment profile allowed by the computer In short, this timer flags a potentially hazardous condition necessitating emergency retraction at 336.

Upon completion of the pre-programmed dwell time for each active wire position at 338, an OK message is sent and a new treatment position is awaited in 339. Control 13 checks to see whether there are further treatment positions for that catheter at 340, if so, the active wire is withdrawn to the specified next adjacent dwell position at 342.

Following the last treatment or dwell position for each catheter, the active wire is fully retracted in 341, checking the overall wire length to confirm that the entire wire length, including the active iridium tip portion, has been properly retrieved. The control 13 thereafter determines by communication 342 with computer 22 whether there are additional catheter treatment profiles to be run at 344. If not, a normal stop at 346 and return to the main menu of computer 22 at 304 occur.

If an additional catheter treatment profile has been programmed, the flow proceeds to block 318 (FIG. 14) and the turret is repositioned and checked at 320. Prior to running each active wire treatment profile, the new catheter position is checked by the dummy wire at 326 as previously described.

What is claimed is:

1. Apparatus for moving a radioactive source formed at the end of a delivery wire into and out of a guide tube connected to a patient for the treatment of said patient, said apparatus comprising:
   a radioactive source formed at an end of a delivery wire;
   a guide tube for connection to a patient;
   means for moving said radioactive source into and out of said guide tube;
   a program controlled control unit means for controlling the treatment of said patient by said radioactive source and, while properly controlling said treatment, for generating periodic reset signals;
   a control unit check timer means, independent of said control unit means, for generating treatment terminate signals at predetermined intervals;
   validity checking means for determining validity of each of said reset signals;
   inhibit means responsive to each of said reset signals determined to be valid by said validity checking means for inhibiting the generation of one of said treatment terminate signals; and
   means responsive to said treatment terminate signals for overriding treatment control by said control unit means and for retracting said radioactive source from said guide tube.

2. The apparatus of claim 1, wherein each reset signal received by said validity checking means is to have a known relationship to the immediately preceding reset signal; and
   said validity checking means comprises means for generating a predicted reset signal value, means for comparing the received reset signal with the predicted reset signal value and means for determining a received reset signal to be valid when the predicted reset signal value equals the received reset signal.

3. The apparatus of claim 2, wherein each reset signal generated by said control unit comprises an N bit binary signal which equals the modulo $2^N$ sum of the last generated reset signal and a predetermined amount and said means for generating a predicted reset signal value comprises means responsive to each received reset signal for adding, modulo $2^N$, said predetermined amount to a stored value representing the preceding reset signal.

4. Apparatus for moving a radioactive source formed at the end of a delivery wire into and out of a guide tube connected to a patient for the treatment of said patient, said apparatus comprising:
   a radioactive source formed at an end of a delivery wire;
   a guide tube for connection to a patient;
   means for moving said source end into and out of said guide tube;
   program controlled control unit means for controlling the treatment of said patient by said radioactive source and, while properly controlling said treatment, for generating periodic reset signals;
   a control unit check timer means comprising a pair of timing circuits, independent of said control unit, each timing circuit for generating treatment terminate signals at substantially the same predetermined interval;
   means responsive to each of said reset signals for inhibiting both of said timing circuits from generating one of said treatment terminate signals; and
   means responsive to said treatment terminate signals for overriding treatment control by said control unit means and for retracting said radioactive source from said guide tube.

5. Apparatus for moving a radioactive source formed at the end of a delivery wire into and out of a guide tube connected to a patient, for the treatment of said patient, said apparatus comprising:
   a radioactive source formed at the end of a delivery wire;
   a guide tube for connection to a patient;
   means for extending said radioactive source end of said delivery wire into said guide tube;
   means for generating a retract signal specifying the removal of said source end from said guide tube;
   timer means responsive to said retract signal for generating a system fault signal a predetermined period of time after receiving said retract signal;
   retraction means responsive to said retract signal for attempting the retraction of said radioactive source end; and means for inhibiting the generation of said fault signal when said source end is withdrawn from said guide tube within said predetermined period of time.

6. The apparatus of claim 5 comprising a source wire retraction indicator means for generating a success signal when said source wire is successfully withdrawn from said guide tube, and said inhibit means is responsive to said success signal for inhibiting the generation of said fault signal.

7. The apparatus of claim 6 comprising means responsive to said fault signal for generating an audible alarm.

* * * * *

UNITED STATES PATENT AND TRADEMARK OFFICE
CERTIFICATE OF CORRECTION

PATENT NO. : 5,139,473

DATED : August 18, 1992

INVENTOR(S) : Bradshaw et al.

It is certified that error appears in the above-identified patent and that said Letters Patent is hereby corrected as shown below:

At column 2, line 35, change "75" to -- 0.75--.

Signed and Sealed this

Twenty-eighth Day of September, 1993

Attest:

BRUCE LEHMAN

*Attesting Officer*          *Commissioner of Patents and Trademarks*